US009764976B2

(12) United States Patent
Pardo

(10) Patent No.: US 9,764,976 B2
(45) Date of Patent: Sep. 19, 2017

(54) PROCESS FOR REDUCING THE PRODUCTION OF SLUDGE BY MUNICIPAL OR INDUSTRIAL WASTEWATER PURIFICATION PLANTS, AND EQUIPMENT FOR THE IMPLEMENTATION THEREOF

(71) Applicant: DEGREMONT, Paris la Defense (FR)

(72) Inventor: Pierre-Emmanuel Pardo, Orsay (FR)

(73) Assignee: DEGREMONT (FR)

( * ) Notice: Subject to any disclaimer, the term of this patent is extended or adjusted under 35 U.S.C. 154(b) by 0 days.

(21) Appl. No.: 14/417,219

(22) PCT Filed: Jul. 25, 2013

(86) PCT No.: PCT/IB2013/056107
§ 371 (c)(1),
(2) Date: Jan. 26, 2015

(87) PCT Pub. No.: WO2014/016797
PCT Pub. Date: Jan. 30, 2014

(65) Prior Publication Data
US 2015/0210577 A1    Jul. 30, 2015

(30) Foreign Application Priority Data

Jul. 26, 2012 (FR) .................................... 12 57253

(51) Int. Cl.
*C02F 9/00* (2006.01)
*C12M 1/34* (2006.01)
(Continued)

(52) U.S. Cl.
CPC ................ *C02F 9/00* (2013.01); *C02F 3/006* (2013.01); *C02F 3/1221* (2013.01); *C02F 3/28* (2013.01);
(Continued)

(58) Field of Classification Search
CPC .. C02F 1/36; C02F 11/00; C02F 11/04; C02F 11/12; C02F 9/00; C02F 3/00; C02F 3/02;
(Continued)

(56) References Cited

U.S. PATENT DOCUMENTS 3,806,448 A * 4/1974 Smith ...................... C02F 3/30
                                                           210/195.3
4,246,099 A * 1/1981 Gould ...................... C02F 3/30
                                                           210/603
(Continued)

FOREIGN PATENT DOCUMENTS

DE          19527784          1/1997
DE          10107712          9/2002
(Continued)

OTHER PUBLICATIONS

Corresponding International Search Report for PCT/IB2013/056107 dated Jan. 27, 2015.
(Continued)

*Primary Examiner* — Katherine Zalasky
*Assistant Examiner* — Benjamin Lebron
(74) *Attorney, Agent, or Firm* — The Belles Group, P.C.

(57) ABSTRACT

A process for reducing the production of sludge by municipal or industrial wastewater purification plants, comprising a step of mesophilic or thermophilic anaerobic digestion (20), or anaerobic digestion combining these two operating modes, of a stream of sludge to be treated (1), and at least one biological solubilization anaerobic treatment step (30); the process comprises, upstream of the anaerobic digestion step, a step of dehydration (10) of the sludge to be treated, followed by a step of mixing (15) the dehydrated sludge with a recirculated fraction of sludge that is more liquid, originating from recycling of the digestion (20), and/or from the
(Continued)

anaerobic treatment step (30), and/or centrates originating from a final dehydration (50) of the treated sludge, wherein the recirculation rate is chosen such that the mixture has a dryness suitable for digestion, this mixture then being directed towards the digestion.

13 Claims, 1 Drawing Sheet

(51) Int. Cl.

| | | |
|---|---|---|
| C12M 1/107 | (2006.01) | |
| C02F 3/28 | (2006.01) | |
| C02F 3/30 | (2006.01) | |
| C02F 3/12 | (2006.01) | |
| C02F 3/00 | (2006.01) | |
| C02F 3/02 | (2006.01) | |
| C02F 11/04 | (2006.01) | |
| C02F 11/12 | (2006.01) | |
| C12M 1/00 | (2006.01) | |

(52) U.S. Cl.
CPC ............... *C02F 3/30* (2013.01); *C12M 21/04* (2013.01); *C12M 41/12* (2013.01); *C12M 41/26* (2013.01); *C02F 3/02* (2013.01); *C02F 3/12* (2013.01); *C02F 3/2893* (2013.01); *C02F 3/308* (2013.01); *C02F 11/04* (2013.01); *C02F 11/127* (2013.01); *C02F 2209/02* (2013.01); *C02F 2209/06* (2013.01); *C02F 2209/14* (2013.01); *C02F 2209/15* (2013.01); *C02F 2209/40* (2013.01); *C02F 2301/046* (2013.01); *C02F 2301/10* (2013.01); *C02F 2301/106* (2013.01); *C02F 2303/10* (2013.01); *C02F 2303/12* (2013.01); *C12M 29/06* (2013.01); *Y02E 50/343* (2013.01); *Y02W 10/15* (2015.05); *Y02W 10/30* (2015.05)

(58) Field of Classification Search
CPC .......... C02F 3/28; C02F 3/1221; C02F 3/308; C02F 3/30; C02F 3/006; C02F 3/2893; C02F 3/12; C02F 11/127; C02F 2209/02; C02F 2209/06; C02F 2209/14; C02F 2209/15; C02F 2209/40; C02F 2301/10; C02F 2301/106; C02F 2301/046; C02F 2303/106; C02F 2303/10; C02F 2303/12; C12M 41/12; C12M 41/26; C12M 21/04; C12M 29/06; Y02E 50/343; Y02W 10/15; Y02W 10/30

See application file for complete search history.

(56) References Cited

U.S. PATENT DOCUMENTS

| | | | | |
|---|---|---|---|---|
| 6,015,496 | A * | 1/2000 | Khudenko | C02F 3/006 210/603 |
| 6,325,935 | B1 * | 12/2001 | Hojsgaard | C02F 11/04 165/299 |
| 2006/0256645 | A1 | 11/2006 | Jensen et al. | |
| 2008/0283468 | A1 * | 11/2008 | Logan | B01F 3/04517 210/603 |
| 2010/0213121 | A1 | 8/2010 | Miller, III | |
| 2011/0056260 | A1 * | 3/2011 | Lemaire | B09B 3/00 71/9 |
| 2011/0203992 | A1 * | 8/2011 | Liu | C02F 1/286 210/607 |

FOREIGN PATENT DOCUMENTS

| | | |
|---|---|---|
| EP | 0620273 | 10/1994 |
| JP | 2007021413 | 2/2007 |
| WO | 2006029971 | 3/2006 |
| WO | 2006124781 | 11/2006 |

OTHER PUBLICATIONS

Corresponding International Search Report for PCT/IB2013/056107 dated Nov. 28, 2013.

\* cited by examiner

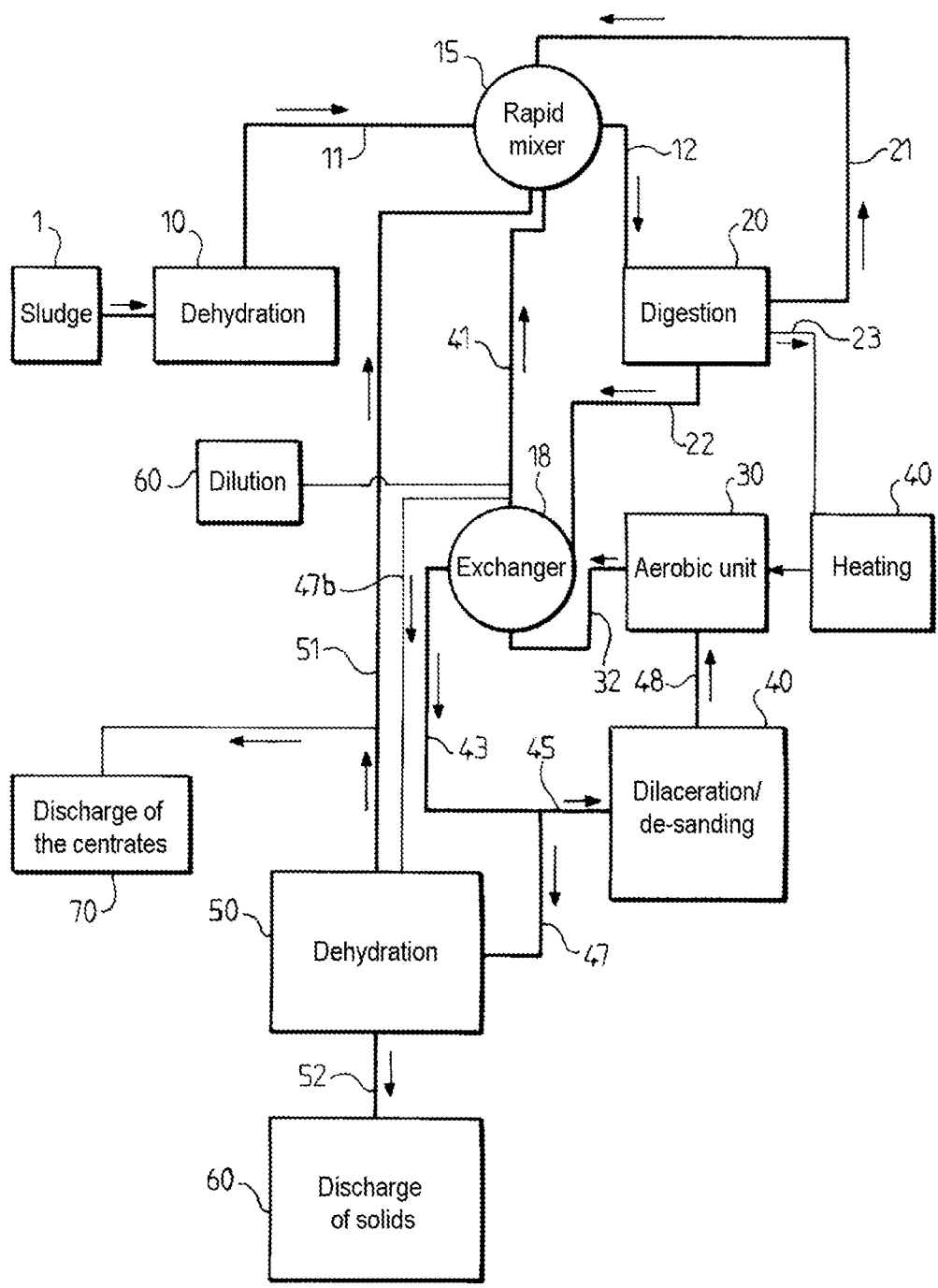

PROCESS FOR REDUCING THE PRODUCTION OF SLUDGE BY MUNICIPAL OR INDUSTRIAL WASTEWATER PURIFICATION PLANTS, AND EQUIPMENT FOR THE IMPLEMENTATION THEREOF

PRIORITY

Priority is claimed as a national stage application, under 35 U.S.C. §371, to international application No. PCT/IB2013/056107, filed Jul. 25, 2013, which claims priority to French application FR1257253, filed Jul. 26, 2012. The disclosures of the aforementioned priority applications are incorporated herein by reference in their entirety.

The present invention relates to a process for reducing the production of sludge by municipal or industrial wastewater purification plants, of the type which comprise a step of mesophilic or thermophilic anaerobic digestion, or digestion which associates these two operating modes, of a flow of sludge to be treated, and at least one aerobic treatment step of biological solubilization of the sludge.

A process of this type is known, in particular from FR 2 849 019. According to this prior process, aerobic treatment with thermophilic enzymatic stress is applied to the digested sludge, in particular from 60 to 70° C. for 24 to 72 hours, which, according to the stress conditions, makes it possible to obtain solubilizations of 20 to 40% of the organic material and 5 to 25% of the mineral material contained in the sludge obtained from the anaerobic digestion process, and to return part of this sludge to the digester. However, this process has several disadvantages, including those which are described hereinafter:

If it is wished to force the treatment, it is necessary to recirculate a large quantity of liquid, thus requiring an oversized reactor allocated to the digestion, which is based in particular on a hydraulic retention time.

The thermophilic enzymatic stress transforms the organic nitrogen into nitrates. These nitrates are a strong pollutant for the digestion. There is therefore a high risk of pollution if it is wished to force the treatment.

Finally, if the thermophilic enzymatic stress step is positioned upstream from the digestion, the production of biogas is not increased significantly, and only the reduction of the production of sludge takes place.

Consequently, the objective of the present invention is above all to provide a process for reducing the production of sludge by municipal or industrial wastewater purification plants anaerobically, which no longer has, or has to a lower degree, the aforementioned disadvantages. In particular, it is desirable to limit or reduce the dimensions of the reactor necessary for the digestion, while increasing the production of biogas.

According to the invention, the process for reducing the production of sludge by municipal or industrial wastewater purification plants comprises a step of mesophilic or thermophilic anaerobic digestion, or digestion which associates these two operating modes, of a flow of sludge to be treated, and at least one aerobic treatment step of biological solubilization, and is characterized in that it comprises, upstream from the anaerobic digestion step:

a step of dehydration of the sludge to be treated;
followed by a step of mixing dehydrated sludge with a recirculated fraction of sludge that is more liquid obtained from recycling of the digestion, and/or from the aerobic treatment step, and/or from centrates and/or from sludge originating from final dehydration of the treated sludge, the level of recirculation being selected such that the mixture has dryness suitable for the digestion, this mixture then being directed towards the digestion.

Preferably, the level of recirculation is also selected such that the concentrations of nitrates of the mixture are suitable for the digestion.

Advantageously, the dryness of the sludge at the output of the first dehydration step is between 20 and 30% by weight of dry materials, and the level of recirculation is selected such that the dryness of the sludge at the output of the mixture and at the input of the digestion is less than 10% by weight of dry materials, and preferably approximately 6%.

Preferably, the aerobic treatment step of biological solubilization is situated downstream from the anaerobic digestion, in particular on a recirculation loop of the anaerobic digestion step.

As far as the aerobic step is concerned, it is possible in particular to implement the technique described in EP-A-924 168 or EP-A-1 008 558. It is also possible simply to put into place an aerated basin without heat, but the global reaction is less substantial.

The aeration of the digested sludge makes it possible to make other bacteria intervene which will "cut" the molecules with C—O bonds. These bonds will then be used during the digestion in order to continue to degrade the organic material. The aerobic step thus makes it possible to force the digestion.

The dehydration step upstream from the digestion makes it possible to eliminate problems of volume of the digester.

The process can comprise a final step of dehydration, in particular by centrifuging.

Advantageously, the process comprises a measurement of nitrates at the input of the digestion, a measurement of ammonium and pH at the output of the digestion, and regulation of the recirculation on the basis of these measurements.

The process can also comprise a step of dilaceration/desanding of the sludge, thus making it possible to decrease the silting up of the digester, the abrasion of the components, and the agglomeration of fibers in the circuit.

Part of the biogas produced during the anaerobic digestion of the sludge can be used as a source of energy to heat or maintain the temperature of a reactor in which the aerobic step of biological solubilization is carried out.

Advantageously, heat exchange takes place between the sludge which is discharged from the aerobic step of biological solubilization and the sludge which is discharged from the anaerobic digestion step, and is directed to the aerobic step, in order for the process to be energetically self-balanced, and for the energy consumption to be reduced. The exchange of heat can be of the indirect sludge/water, water/sludge type, with the water acting as a heat-exchanging fluid for the exchange between the two sludges.

Preferably, dilution is provided on a recirculation loop which is connected to the aerobic step output, in order to make it possible to control the operating conditions of the digestion.

Return flows obtained from the aerobic step or from final dehydration can be controlled, in particular according to the operating conditions of the digestion and of the production of biogas, and according to the quality of the solid residue (levels of volatile materials and nitrogen).

Since, according to the invention, firstly the process for reducing the production of sludge is implemented on the sludge treatment line, and secondly, because it comprises a dehydration step initially, it conveys little water, it is independent from the water treatment line, and does not lead to significant modifications of the operation of this water treatment line.

In addition, since the organic material which is solubilized during the aerobic step is degraded anaerobically in the process according to the invention, this degradation does not lead to excess consumption of oxygen on the water treatment line, and therefore does not result in any increase in the supply of oxygen on this water treatment line.

On the other hand, on the water treatment line, account must be taken of the increase in nitrates returned from the head.

According to these different modes of implementation, the present invention makes it possible to increase by to 50% the kinetics of production of biogas, and makes it possible to increase by 30 to 100% the performance of degradation of the organic materials contained in the sludge, in comparison with a conventional process for anaerobic digestion of the sludge.

The present invention makes it possible to improve significantly the reduction of the concentration of pathogenic microorganisms in the effluent sludge, and also to eliminate partly or completely filamentary microorganisms which are responsible for the foaming phenomenon in the anaerobic digestion step.

In addition, implementation of the process according to the invention permits improvement of the dryness of the sludge of between 20 and 40% in comparison with the conventional anaerobic digestion processes.

The process according to the invention is energetically self-balanced, and, according to these different modes of implementation, part of the biogas which is produced during the anaerobic digestion of the sludge is used as a source of energy to heat or maintain the temperature (50 to 70° C.) of the reactor in which the aerobic step takes place.

According to the present invention, and as in FR 2 849 019, the process can comprise a step of secondary dephosphatation which is implemented in the circuit for reduction of the production of the sludge, as a complement to that which is implemented in the main water treatment line. In this case, the phosphorous pollution is eliminated by chemical precipitation, by addition of metal salts and/or mineral compounds.

The invention also relates to an installation for implementation of the process, this installation comprising an anaerobic digester of the mesophilic or thermophilic type, or a digester which associates these two operating modes, of a flow of sludge to be treated, and at least one reactor for aerobic treatment of biological solubilization of the sludge, and being characterized in that it comprises, upstream from the anaerobic digester:
  a device for dehydration of the sludge to be treated;
  followed by a mixer to mix dehydrated sludge with a recirculated fraction of sludge that is more liquid, supplied by a recycling duct originating from the digester, and/or by a duct originating from the aerobic treatment reactor, and/or by a centrates duct, and/or by a fraction of the solid sludge originating from final dehydration of the sludge treated, the level of recirculation being selected such that the mixture has dryness suitable for the digestion, and that the concentrations of nitrates are suitable for the digestion, the mixture then being directed towards the digestion.

Advantageously, the aerobic treatment reactor is situated downstream from the anaerobic digester, in particular on a recirculation loop of the anaerobic digester.

The installation can comprise a final dehydration device, in particular a centrifuge. The installation can also comprise a device for dilaceration/de-sanding of the sludge, thus making it possible to decrease the silting up of the digester, the abrasion of the components, and the agglomeration of fibers in the circuit.

Preferably, the installation comprises a device for heating of the aerobic reactor, supplied by part of the biogas produced by the anaerobic digester of the sludge.

The installation can comprise a sensor for nitrates at the input of the digester and a sensor for ammonium (ammonium ion NH4+) and pH at the output of the digester. These sensors make it possible to control the recycling operations better.

The installation can comprise a heat exchanger between sludge which is discharged from the aerobic reactor and sludge which is discharged from the anaerobic digester and is directed to the aerobic reactor.

The installation advantageously comprises a dilution device which is provided on a recirculation loop originating from the output of the aerobic reactor, in order to make it possible to control the operating conditions of the digestion.

In addition to the above-described provisions, the invention consists of a certain number of other provisions, which will be described in greater detail hereinafter in relation to an embodiment which is described with reference to the appended drawing, but is in no way limiting. In this drawing:

The sole FIGURE is a schematic representation of an installation which implements the process for reducing the production of sludge according to the invention, in association with the dehydration, the anaerobic digestion step, and the aerobic step.

The FIGURE of the drawing shows a sludge treatment installation according to the present invention, which comprises upstream a device 10 for dehydration of the sludge 1 to be treated, originating from a municipal or industrial water treatment line. This device 10 can be a band filter, a centrifuge, a press filter, or any other dehydration equipment which makes it possible to increase the dryness of the sludge significantly. The greater the dryness, the greater the cost savings of the process as a whole will be. Typically, the level of dryness to be obtained will be 20 to 30% of dry materials at the output of the dehydration device 10. The dehydration can involve all of the flow of sludge or only part of it, the other part being derived from a duct (not represented) which bypasses the device 10.

The installation which implements the process according to the invention is advantageously independent from the wastewater treatment line; the sludge produced in the water treatment line is transported or transferred to the installation according to the invention.

The output of the dehydration device 10 is connected by a duct 11 to the input of a rapid mixer 15 which makes it possible to produce a thoroughly mixed and homogenous mixture of the dehydrated sludge obtained from the dehydration 10, that obtained from another dehydration process 50; and:
  diluted sludge obtained from a reactor or digester which provides the digestion, this sludge being recirculated by a duct 21 which connects an output of the digester 20 and an input of the mixer 15; the direction of flow of the sludge in the duct 21 is indicated by an arrow; this recirculation 21 permits in particular maintenance of the temperature of the digester 20 by means of an exchanger, not represented, if necessary;
  and/or sludge treated aerobically in an aerobic reactor 30, this sludge reaching the mixer 15 via a duct 41;

and/or the centrate, or liquid fraction, recirculated by a duct 51 which leads to the mixer 51, and originates from the final dehydration step 50, in particular by centrifuging.

It should be noted that, according to the qualities of sludges, the duct 51 can be designed to transport either centrates or dehydrated sludge. If it is necessary to transport both for reasons of regulation of the process, two sets of piping 51 can be implemented (not represented).

Units for measurement and regulation of the flow, in particular solenoid valves, not represented, are provided on the different ducts, in particular 21, 41, 51, in order to regulate the respective flows, in particular according to the flow in the duct 11. The directions of flow in the ducts are indicated by arrows along these ducts.

Measurement and regulation units (not represented) are also provided on the different ducts, in particular a nitrates sensor on the duct 12, and an ammonium and pH sensor on the duct 22, which provide measurement results to a regulator (not represented) which makes it possible to regulate the recirculations.

According to the different flows, a plurality of mixing configurations can be provided between the flow of the duct 11 on the one hand, and the flows of the ducts 21, 41, 51 on the other hand.

The mixing configurations are designed such that the sludge which is discharged from the mixer 15 by the duct 12 which is connected to the input of the digester has dryness suitable for the digestion, in particular dryness of 6% or less, such that the viscosity of the sludge is suitable for the digestion. The mixer 15 can be of the rapid mixing type (flash-mixing), with high coefficients of mixing.

The device 20 for anaerobic digestion of the sludge is of a type which can implement an anaerobic digestion process which is mesophilic or thermophilic, or which associates these two operating modes (with or without an acidogenesis step).

The aerobic reactor 30, which is of a size suitable for retention times of 4 to 96 hours, is maintained at a temperature which can range from ambient temperature of 20° C., to 75° C., and preferably at a temperature from 60 to 70° C. which assists the reactions. This reactor can be heated by a heating device 40, to which part of the biogas produced by the anaerobic digester 20 of the sludge is supplied as fuel by a duct 23. Any other means for recuperation of energy can be provided for the heating, in particular a sludge/sludge exchanger 18, or a sludge/water or water/sludge exchanger.

The reactor 30 is aerated by insufflation of air or oxygen by means of nozzles (not represented) which are disposed in the base of the reactor. The supply of oxygen to the reactor 30 is at least equal to that necessary to ensure the stoichiometry of the oxidation of the materials to be treated; preferably, the oxygen supply is greater than the stoichiometric value, and is classified as super-stoichiometric.

An output of the digester 20 is connected to a duct 22 which directs the digested sludge to the input of the aerobic reactor 30. Preferably, the duct 22 is connected to the input of a first circuit of a heat exchanger 18, the output of this first circuit being connected to a duct 43. The other circuit of the exchanger 18 comprises an input which is connected by a duct 32 to the output of the aerobic reactor 30, and an output which is connected by a duct 41 to the mixer 15.

The sludge which is discharged from the reactor 30 by the duct 32 contributes towards heating up in the exchanger 18 the sludge originating from the duct 22 of the digester 20.

This exchanger unit 18 can consist of a sludge/water, water/sludge exchanger where the water acts as a medium to transfer the heat from the sludge in the duct 32 to the sludge in the duct 22.

The duct 43 is divided into two branches formed by ducts 45, 47. The duct 45 is connected to the input of a dilaceration/de-sanding device 40, which makes it possible to remove the sand from the sludge, for example by hydrocyclonic treatment, and to eliminate clumps of fibers. The output of the device 40 is connected by a duct 48 to the input of the aerobic reactor 30.

A recirculation loop 22, 43, 45, 48, 32, 41, 12 of the anaerobic digester 20 is formed, on which the aerobic reactor 30 is installed between the ducts 48 and 32. The aerobic reactor 30 is supplied only by digested sludge originating from the digester 20.

The duct 47 is connected to the input of a device 50 for dehydration of the treated sludge, which can be a band filter, a centrifuge, a press filter, or any other means for forced dehydration of the sludge.

It should be noted that, in another configuration, not represented, the cooled sludge at the output of the aerobic reactor 30 can also be directed to the dehydrator 50, from the duct 41, before the dilution 60.

Recirculation of the aerated sludge discharged from the reactor 30 to the digester 20 is ensured by the ducts 32, 41 and 12, according to the direction of flow indicated by arrows. This recirculation trajectory optionally, but advantageously, comprises the exchanger 18, which ensures cooling of the sludge discharged from the aerobic reactor 30, in order to preheat the sludge originating from the digester 20, and being directed to the aerobic reactor 30.

A dilution device 60, which is connected to the duct 41, is designed to permit injection of a liquid, generally water, in order to control the operating conditions of the digester 20, which requires relatively low dryness of the sludge, of approximately 6% of dry materials, for satisfactory operation.

Recirculation of part of the centrates, i.e. the liquid fraction of the dehydration 50, is provided by means of a duct 51 which connects the output of the centrates to the mixer 15. This recirculation contributes towards controlling the dilution and treatment of the organic materials which are still solubilized. It should be noted that, according to the quality of the sludge to be treated, the duct 51 can have dimensions such as, rather, to recirculate the solid sludge, which also contains the organic material.

The output for the non-recirculated solid fraction from the dehydration device 50 is connected by a duct 52 to a unit 60 for discharge of the solid fraction.

The output for the liquid fraction from the duct 51 also opens towards a unit 70 for discharge of the centrates which generally return to the plant.

The installation is equipped with pumping means, means for measurement, and regulation units (not represented) in order to provide all the flows, controls and regulations which permit control of the process, and in particular the controls and regulations:

- of the operating parameters of the digester 20, i.e. temperature, hydraulic load, mass load, concentration, pH, etc.;
- of the operating parameters of the aerobic step 30, i.e. temperature, load, etc.;
- of the level of recirculation of the different flows by the ducts 21, 41, 51;
- of the level of nitrates and ammonium in the digester.

According to the configuration implemented in the FIGURE of the drawing, the process which is the subject of the present invention makes it possible, by means of the aerobic treatment, to limit in the anaerobic digestion step the phenomena of foaming caused by the presence of filamentary microorganisms.

In addition, these configurations make it possible to improve by 1 to 20 points the dryness of the residual sludge after dehydration treatment, in comparison with conventional anaerobic digestion.

The installation functions as follows.

The sludge 1 to be treated is subjected to dehydration in the device 10, in order to have at the output dryness of at least 20 to 30% of dry materials. A substantial part of the water in the sludge 1 has been eliminated, such that the volume of sludge to be treated by the digester 20 is reduced, and the dimensions of the digester 20 are reduced substantially accordingly.

However, a level of dryness of this type is too high for satisfactory functioning of the digester 20. The recirculation of solubilized sludge originating from the digester 20, via the duct 21, and/or from the aerobic reactor 30, via the duct 41, and/or from the final dehydration device 50, via the duct 51, makes it possible to obtain at the output of the mixer 15, in the duct 12, a sludge with dryness which is suitable for the digestion, and generally dryness of approximately 6% by weight of dry materials. The level of recirculation is selected such as to obtain this dryness at the input of the digester 20.

The sludge is digested and solubilized partly in the digester 20. Part of the digested sludge is recycled via the duct 21, as previously described; the other part is discharged via the duct 22, then the duct 43. The flow is then separated between the duct 45 and the duct 47. The duct 45 directs the flow towards the dilaceration/de-sanding device 40. The flow is discharged via the duct 48, in order to enter the reactor 30, and to undergo aeration treatment there, preferably thermal aeration at approximately 60-70° C. The sludge which is treated in the reactor 30 is discharged via the duct 32, and is directed via the duct 41 to the mixer 15.

The duct 47 directs the sludge to the final dehydration device 50. The centrates, or liquid fraction, from the device 50 are directed to the mixer 15, whereas the solid fraction is directed at least partly, via the duct 52, to the discharge 60. A fraction of the centrates is discharged from the system, from the duct 51, to the discharge 70. A duct 47b also makes it possible to direct part of the sludge from the duct 41 to the dehydration device 50.

The dehydration which is provided by the device 50 makes it possible to avoid a concentration of the nitrates produced in the aerobic reactor 30 and the ammonia produced by the digestion. In fact, the nitrates at the output of the aerobic reactor are in liquid form. By passing into the dehydration device 50, they are purged together with the centrates discharged at 70. The ammonia produced by the digester is also in liquid form; it can either be purged directly at 47 by means of the dehydration device 50 and the discharge of the centrates 70, or transformed into nitrates in the aerobic step 30.

When the installation is started up, the retention time of the sludge in the digester 20 is longer than in continuous operation, until the recycled solubilized sludge makes it possible to obtain the required dryness at the input of the digester 20.

By means of the process according to the invention:
the dimensions of the digester 20 are reduced in comparison with those of a digester according to the prior art;
the output of the digestion is improved;
the final production of sludge is decreased, since the organic material is transformed more into carbon dioxide and methane;
the ammonia and nitrates are purged.

The invention claimed is:

1. A process for reducing the production of sludge by municipal or industrial wastewater purification plants, comprising:
    a first dehydration step receiving a flow of sludge to be treated;
    a step of mesophilic or thermophilic anaerobic digestion, or digestion which associates these two operating modes, of the flow of sludge to be treated, the step of mesophilic or thermophilic anaerobic digestion being downstream of the first dehydration step;
    at least one aerobic treatment step of biological solubilization downstream from the step of mesophilic or thermophilic anaerobic digestion;
    a final dehydration step; and
    a step of mixing between the first dehydration step and the step of mesophilic or thermophilic anaerobic digestion, to mix dehydrated sludge with a recirculated fraction of sludge that is more liquid obtained from recycling of one or more of the step of mesophilic or thermophilic anaerobic digestion, the aerobic treatment step, centrates, and sludge originating from the final dehydration step of the treated sludge, a level of recirculation being selected such that the mixture has dryness suitable for the step of mesophilic or thermophilic anaerobic digestion, the mixture then being directed towards the step of mesophilic or thermophilic anaerobic digestion,
    wherein sludge discharged from the step of mesophilic or thermophilic anaerobic digestion is divided between first and second branches, the first branch connected to the aerobic treatment step to direct a first fraction of sludge discharged from the step of mesophilic or thermophilic anaerobic digestion to the aerobic treatment step and the second branch directly connected to the final dehydration step to direct a second fraction of sludge discharged from the step of mesophilic or thermophilic anaerobic digestion to the final dehydration step.

2. The process as claimed in claim 1, wherein the dryness of the sludge at an output of the first dehydration step is between 20% and 30% by weight of dry materials, and the level of recirculation is selected such that the dryness of the sludge at an output of the mixture and at an input of the step of mesophilic or thermophilic anaerobic digestion is less than 10% by weight of dry materials.

3. The process as claimed in claim 1, wherein the aerobic treatment step of biological solubilization is situated on a recirculation loop of the step of mesophilic or thermophilic anaerobic digestion.

4. The process as claimed in claim 1, wherein the final dehydration step is achieved by centrifugation.

5. The process as claimed in claim 1, further comprising a measurement of nitrates at an input of the step of mesophilic or thermophilic anaerobic digestion, a measurement of ammonium and pH at an output of the step of mesophilic or thermophilic anaerobic digestion, and regulation of the level of recirculation on the basis of these measurements.

6. The process as claimed in claim 1, further comprising a step of dilaceration/de-sanding of the sludge to decrease silting up of a digester used for the step of mesophilic or thermophilic anaerobic digestion, abrasion of components, and agglomeration of fibers.

7. The process as claimed in claim 1, wherein part of a biogas produced during the step of mesophilic or thermophilic anaerobic digestion of the sludge is used as a source of energy to heat or maintain the temperature of a reactor in which the aerobic treatment step of biological solubilization is carried out.

8. The process as claimed in claim 1, wherein heat exchange takes place between the sludge which is discharged from the aerobic treatment step of biological solubilization and the sludge which is discharged from the step of mesophilic or thermophilic anaerobic digestion in order for the process to be energetically self-balanced, and for the energy consumption to be reduced.

9. The process as claimed in claim 8, wherein the exchange of heat is of the indirect sludge/water, water/sludge type, with water acting as a heat-exchanging fluid for the exchange between the two sludges.

10. The process as claimed in claim 1, wherein dilution is provided on a recirculation loop which is connected to an output of the aerobic treatment step for controlling operating conditions of the step of mesophilic or thermophilic anaerobic digestion.

11. The process as claimed in claim 1, wherein return flows obtained from the aerobic treatment step or from the final dehydration step are controlled according to operating conditions of the step of mesophilic or thermophilic anaerobic digestion and of production of biogas, and according to a quality of solid residue (levels of volatile materials and nitrogen).

12. The process as claimed in claim 2, wherein the input of the step of mesophilic or thermophilic anaerobic digestion is less than 6% by weight of dry materials.

13. The process as claimed in claim 8, wherein the sludge discharged from the step of mesophilic or thermophilic anaerobic digestion is divided between the first and second branches after the heat exchange.

\* \* \* \* \*